United States Patent [19]

Willis et al.

[11] 3,958,448
[45] May 25, 1976

[54] TEST APPARATUS FOR PRESSURIZED CONTAINER AND METHOD

[75] Inventors: Wilburn C. Willis; William L. Denhart, both of Hagerstown; Frank M. Kelly; Joseph A. Clements, both of Richmond, all of Ind.

[73] Assignee: Aluminum Company of America, Pittsburgh, Pa.

[22] Filed: Oct. 10, 1974

[21] Appl. No.: 513,718

[52] U.S. Cl. ................................. 73/37; 73/49.2; 73/52
[51] Int. Cl.² ...................................... G01M 3/02
[58] Field of Search ............ 73/37, 45.4, 49.2, 49.3, 73/52, 40.7, 41

[56] References Cited
UNITED STATES PATENTS

| | | | |
|---|---|---|---|
| 983,962 | 2/1911 | Werner | 73/52 |
| 1,211,942 | 1/1917 | Hoff | 73/52 |
| 2,697,935 | 12/1954 | Gordon | 73/45.5 X |
| 2,912,852 | 11/1959 | Trinneer | 73/49.2 |
| 3,251,218 | 5/1966 | Russell | 73/52 |
| 3,418,845 | 12/1968 | Helms | 73/45.5 |
| 3,462,996 | 8/1969 | Frank | 73/49.2 X |
| 3,712,112 | 1/1973 | Widmer et al. | 73/37 |
| 3,771,649 | 11/1973 | Strauss | 73/37 X |

*Primary Examiner*—Richard C. Queisser
*Assistant Examiner*—John S. Appleman
*Attorney, Agent, or Firm*—Arnold B. Silverman

[57] ABSTRACT

A pressure testing apparatus for sealed containers including a container receiving enclosure defined by a base wall, a side wall and a top wall. A container supporting pedestal having a needle projecting upwardly therefrom is positioned within the container receiving enclosure. A pressurized fluid supply means is in communication with the needle. An adjustable container retaining member is disposed within the container receiving enclosure in spaced overlying relationship with respect to the container supporting pedestal. Pressure control means are interposed between the pressurized fluid supply means and the needle.

A method of testing a sealed container which includes placing the sealed container within the container receiving enclosure, piercing the container by means of a generally upward projecting needle to establish sealed contact between the needle and the interior of the container. The container is secured in test position by means of an adjustable container retaining member which limits upward movement of the container to an amount insufficient to lift the container entirely off the needle. Pressurized fluid is subsequently supplied to the interior container and such delivery of pressurized fluid is terminated when the internal pressure reaches a predetermined level or when container failure occurs.

13 Claims, 9 Drawing Figures

TEST APPARATUS FOR PRESSURIZED CONTAINER AND METHOD

BACKGROUND OF THE INVENTION

1. Field of the Invention

This invention relates to the testing of sealed containers having an internal pressure greater than atmospheric and, more specifically, relates to an apparatus and method for such testing which is capable of establishing carefully monitored, predetermined internal pressures within the container tested.

2. Description of the Prior Art

It has been known to provide tests of the security of sealed containers having internal pressures greater than atmospheric. Such needs have been particularly important in connection with packages for foods and beverages. For example, with respect to soft drinks, an internal pressure of about 150 psi may be encountered and, with respect to beer, a pressure of about 100 psi is generally encountered. The premature, undesired failure of the package to effectively maintain the sealed relationship cannot only result in loss of product and spoilage thereof, but also can create a safety hazard. For example, there have been instances wherein bottle closures have been projected through the air with an explosive type action resulting in injury to the person hit by the same.

As a result of increasing concern for not only minimizing, but totally eliminating all instances of human injury as a result of such accidents, convenient, efficient and reliable set procedures have been needed.

With respect to bottle closures, one known means for testing the security of a particular closure on a particular bottle involves the cumbersome procedure of cutting the bottle with the closure intact at a position below the closure. The bottle portion with closure in place was then mounted upon a suitable fixture which was in communication with a source of pressurized fluid such as air. The pressure was progressively increased until such time as closure failure occurred and the pressure at the point of failure was used as an indication of the effectiveness of closure securement and, to a certain extent, the integrity of the seal at different pressure levels. As a result of the need to destroy the package in order to perform such a test, such procedures have generally been regarded as not only being cumbersome and inefficient, but also have failed to provide a test of the full package in its sealed condition.

Another known approach to pressure testing of particular bottle closures has involved the use of a metal fixture made to the dimensions of the particular bottle on which the closure was to be employed. The closure was sealed to the metal fixture and a test procedure similar to that employed in connection with the cut-off bottle described above was used. This approach eliminated the need for cutting a container into two parts, but perpetuated the other disadvantages set forth above. This approach also assumed that all the container sections would, in fact, have the idealized dimensions of the particular metal fixture. In view of the interrelationship between glass or plastic finish tolerances and the dimensions of the metal fixture, in some instances, such assumption was probably not warranted.

We previously have created a pressure testing apparatus for sealed containers which involved placing the container in an inverted position within an enclosure and introducing pressurized air into the container interior by means of a needle which was in communication with a source of pressurized fluid. The container was permitted to move upwardly responsive to the application of pressure sufficiently high to create seal or container failure and an overlying, generally conical member caught the upwardly moving container by frictionally engaging the same. Such system also contemplated the use of bottle holding fixtures which conform to portions of the bottle between the base and the neck thereof and, also, involved the need to bolt or otherwise firmly secure the bottle receiving housing lid so as to resist the upward thrust of the moving bottle. While the general concept of this approach showed promise, the time-consuming manner in which bottles were introduced and removed, the need to have a number of different sized fixtures in complimentary shape with respect to each bottle to be tested, the absence of ready access to the housing interior, the absence of feasibility in respect of use of the equipment for a wide range of types and sizes of containers and the absence of significant safety features which would preclude laboratory or plant personnel from being injured during use of the system, have resulted in limited use of these approaches.

There remains, therefore, a substantial need for an easily used, economical, rapid and reliable test apparatus and method for testing the pressure holding capacity of various types of containers in a system which provides the opportunity to test the precise product which will be going to the marketplace without the need to alter the same prior to testing.

SUMMARY OF THE INVENTION

The present invention has met the above described need by providing an apparatus which is adapted for use with a wide range of types of containers, permits ready insertion and withdrawal of test specimens, permits testing of entire packages and provides significant safety features so as to limit risks assumed by the user. A container-receiving enclosure is provided with a container supporting pedestal which has a generally upwardly projecting needle. A source of pressurized fluid, preferably air or a suitable gas such as nitrogen or carbon dioxide, is in communication with the needle and pressure control means provide progressive increases in internal pressure of the sealed container interior after the needle has pierced through a wall of the container. An overlying container member is adjustable and adapted to resist undesired excessive upward container movement. The adjustable container restraining member may consist of a sleeve-like member engaging the container and a cooperating adjustment post to which the sleeve-like member may be secured at various desired positions. The upper wall of the container receiving enclosure need not serve as the prime element resisting excessive upward movement of the container, but rather, a restraining portion of the container retaining member may accomplish this objective, thereby permitting ease of container insertion and withdrawal. Means are provided for preventing the buildup of pressure within the sealed container prior to full closing of the container receiving enclosure and for preventing opening of the container receiving enclosure prior to reduction in pressure within the same.

The method of this invention involves piercing the container with an upwardly projecting needle in order to establish sealed contact therebetween. The container is secured in position by means of the container retaining member which is so positioned as to limit upward movement of the container to an amount insufficient to lift the container entirely off of the needle. Pressurized fluid, preferably air or a suitable gas or mixture thereof, is then supplied to the interior of the container by means of the needle, while the internal container pressure is monitored. Delivery of pressurized fluid to the interior of the container is terminated either when the internal pressure reaches a predetermined level or when container or closure failure occurs. In containers which are glass or plastic provided with a metal closure, it is preferable to invert the container during testing so that the closure is pierced by the upwardly projecting metal.

It is an object of this invention to provide an apparatus and method for the testing of sealed containers having an internal pressure equal to or greater than atmospheric pressure.

It is another object of this invention to provide such apparatus and method which is adapted for use on a complete sealed container of the type being sent to the marketplace without the need for prior severance of portions thereof.

It is another object of this invention to provide such method and apparatus which may economically be adopted for plant and laboratory locations and will operate in a safe fashion so as to be readily usable by a semi-skilled or unskilled worker.

These and other objects of the invention will be more fully understood from the follow description of the invention on reference to the illustrations appended hereto.

DESCRIPTION OF THE PREFERRED EMBODIMENTS

Figure 1:
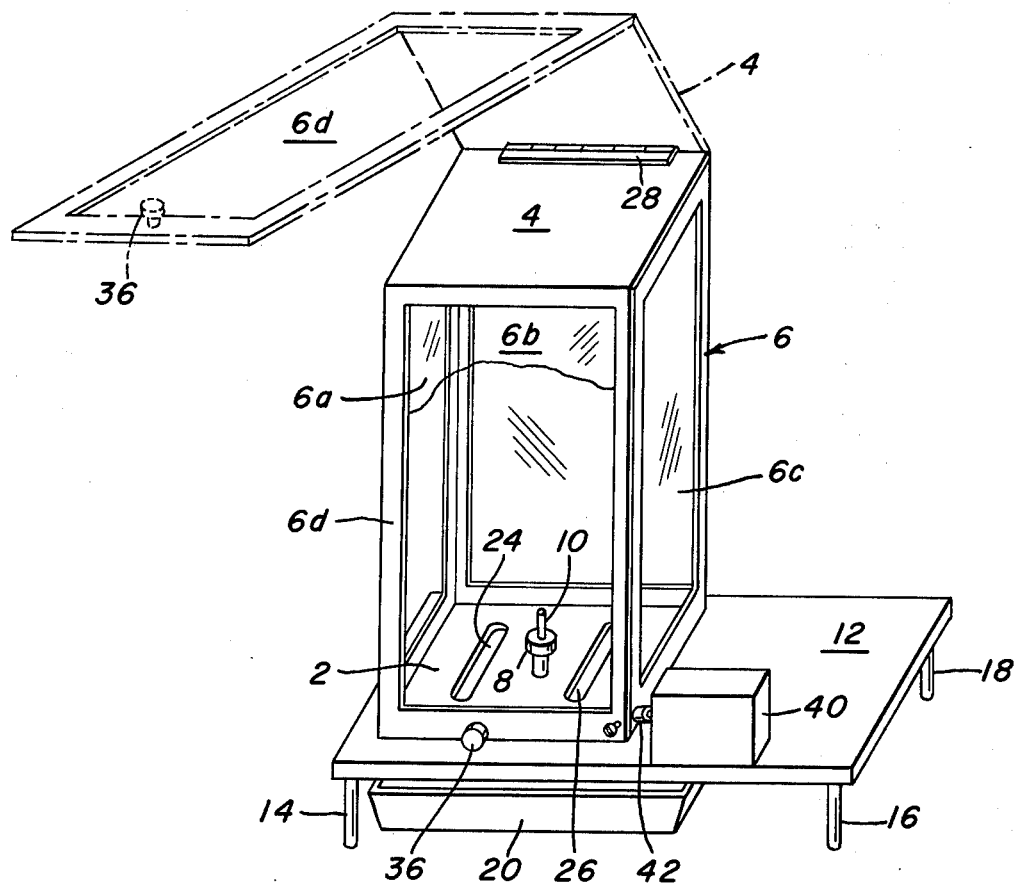
FIG. 1 is a perspective somewhat schematic view of the apparatus of this invention, with portions thereof deleted in the interest of clarity of illustration.

Referring now more specifically to FIG. 1, there is shown a container-receiving enclosure which is defined by a base wall 2, a top wall 4 and a side wall 6. In the form shown, the side wall 6 is composed of four joint sections, 6a, 6b, 6c and 6d. Disposed within the container-receiving enclosure and secured to the base wall 2 thereof is a container-supporting pedestal 8 on which is mounted an upwardly projecting hollow needle 10. In the form illustrated, the side wall sections 6a, 6b, 6c and 6d are composed of a transparent, relatively strong material such as polycarbonate, acrylic or polysulfunate. If desired, however, other materials of suitable strength which are adapted to resist penetration by exploding container fragments may be employed. In instances where it is not necessary or desirable to view the test procedure directly, metals such as stainless steel or aluminum could be employed. Also, while in the preferred embodiment the side wall is composed of a number of joined transparent side wall sections which serve to define a continuous side wall, the side wall might be a unitary member, if desired.

The container-receiving enclosure rests upon a support member 12 which has legs 14, 16, 18 (and at least one additional leg at the corner not illustrated) which serve to place base wall 12 at a position spaced above the table or floor surface on which the apparatus is located. This spacing serves to permit introduction of pressure lines and other equipment and components thereof. In addition, pan 20, which is adapted to receive any liquids emerging from a broken container, is positioned in underlying relationship with respect to base wall 2. While various forms of drainage may be provided, it is preferred to place elongated openings 24, 26 which communicate with the interior of the container-receiving enclosure and the underlying space so as to permit drainage therethrough into pan 20. If desired, a drainage opening (not shown) provided with a suitable cap and adapted to serve as a connection for a drainage hose may be provided in pan 20.

In the embodiment shown, the top wall is secured to rear side wall sector 6b by means of hinge 28 so as to permit ready opening of the container-receiving enclosure and access to the interior thereof. In this form, it is noted that by means of the front side wall sector 6d is formed as a unit with top wall 4 and adapted for movement therewith. Thus, a user may grasp knob 36 and raise the same so as to place the side wall 6d and top wall 4 in the positions indicated by the dotted lines in the top portion of FIG. 1. This permits full access to the container-receiving enclosure from both the front and top. Such full access is particularly desirable in those instances where a container has failed through fracture of a container into small particles. Cylinder 40 has a piston 42 which serves to prevent opening of door or side panel 6d at periods when the sealed container is at pressures which have been increased as a result of the introduction of pressurized fluid into the container interior by this system.

Figure 2:
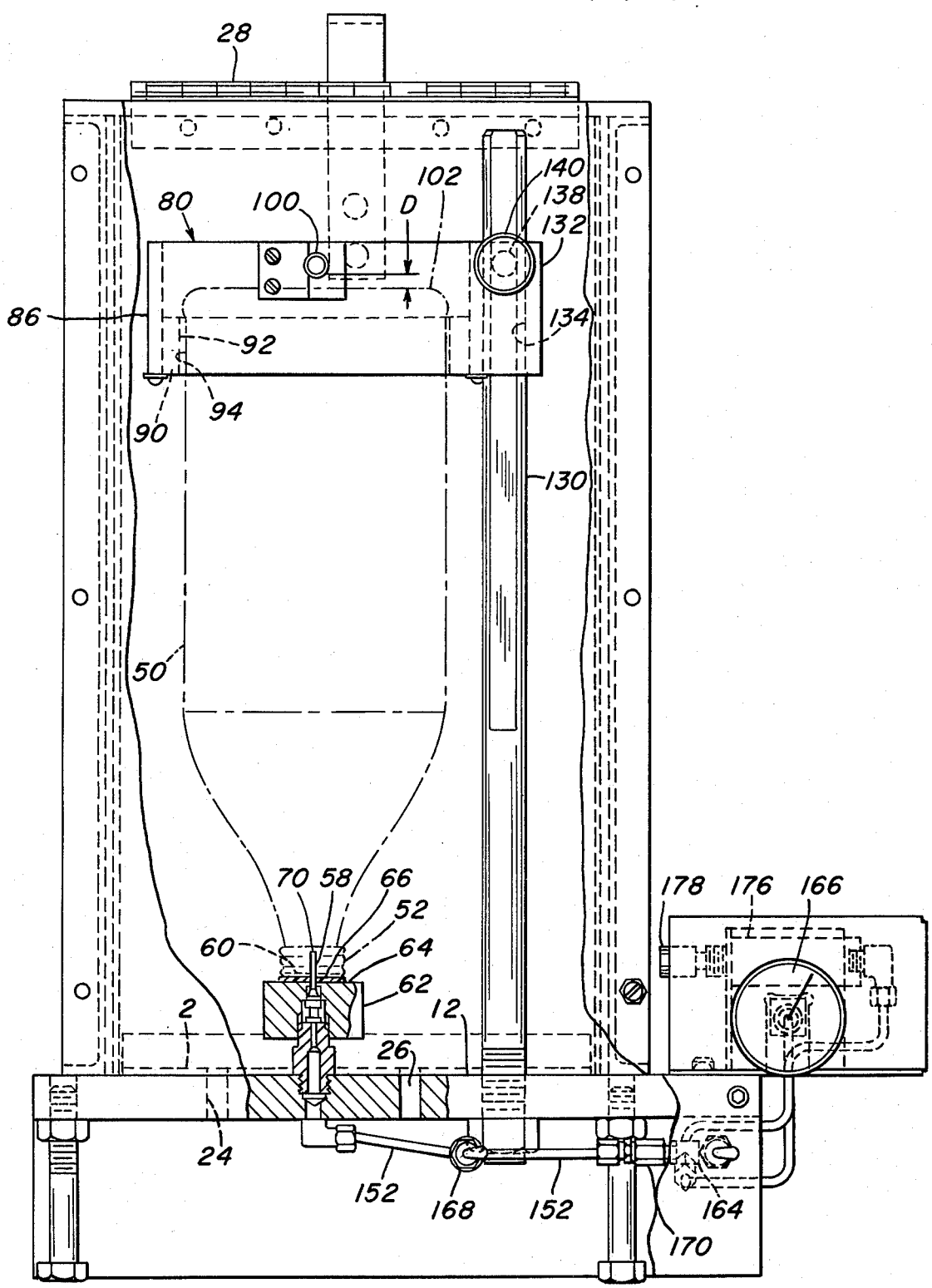
FIG. 2 is a detailed sectional elevation showing a preferred embodiment of the present invention with a sealed bottle in test position.
Figure 4:
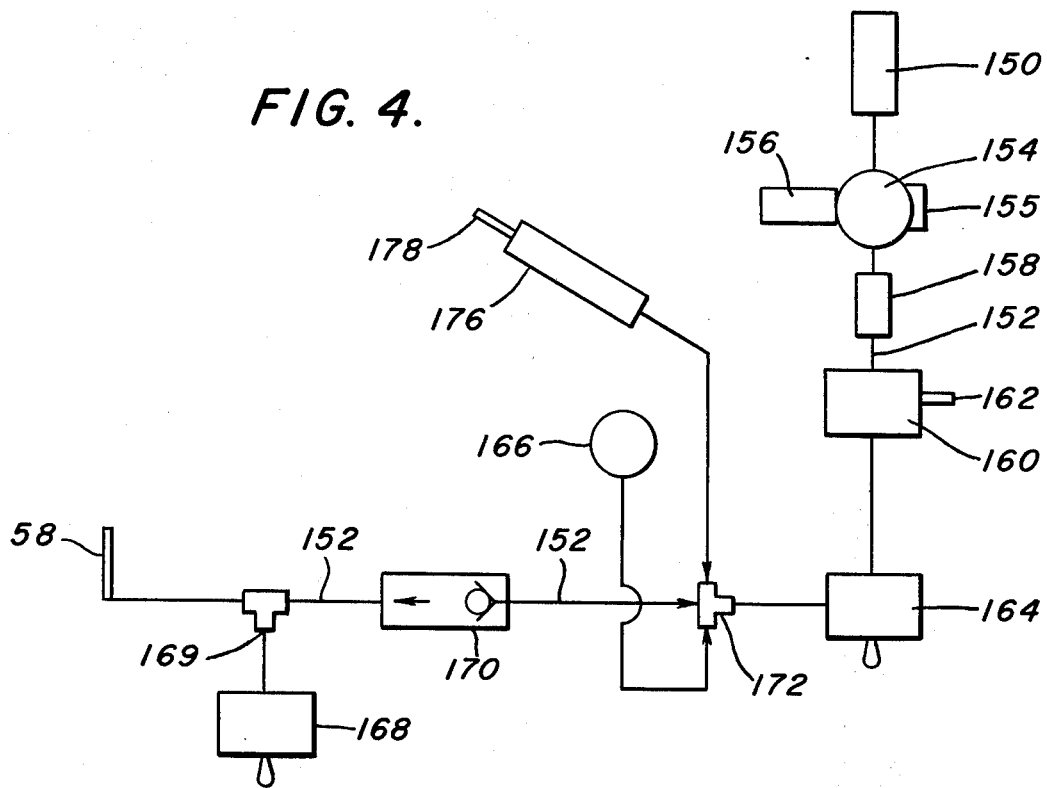
FIG. 4 is a schematic illustration of the pressurized fluid-handling system of the present invention.

Referring now more specifically to FIGS. 2 and 4, it is seen that a sealed container 50, which in this instance is a bottle, has a threaded closure 52 sealingly secured thereto and is disposed within the container-receiving enclosure in inverted position. In the form shown, needle 58 has pierced end wall 60 of closure 52 and is in communication with the container interior. The container-supporting pedestal 62 has an upwardly facing container-supporting surface 64 which will facilitate support of the container thereon. In the form illustrated, a gasket element 66 is disposed on upper surface 64 in surrounding relationship with respect to a portion of needle 58 and thereby contributes to the sealed relationship between the needle 58 and the container interior.

Figure 5:
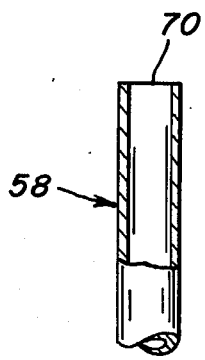
FIG. 5 is a fragmentary sectional illustration of the end portion of a needle employed in this invention.
Figure 6:
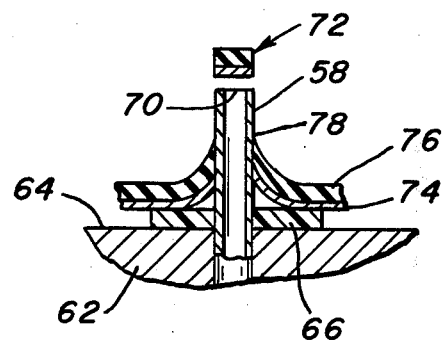
FIG. 6 is a fragmentary cross-sectional illustration of a needle and the adjacent portions of a container wall which has been pierced.

Referring now briefly to FIGS. 5 and 6, a preferred aspect of needle construction will now be considered. The portion of the needle 58 shown in FIG. 5 has a longitudinal axis which runs generally vertically and a free end 70 which provides an edge which is in a plane oriented generally perpendicular with respect to the longitudinal axis of the needle 58. This sort of orientation is preferred as it has been found that if the edge lies in a plane which creates a substantial angle between the plane perpendicular to the longitudinal axis of the needle and the plane in which it lies, i.e., an angle above about 15°, the tendency is to create an irregular opening within the container wall and preclude the existence of an effective seal which is desired in order to permit increasing container internal pressure. As is shown in FIG. 6, it has been found that a needle edge 70 which is in a plane generally perpendicular to the longitudinal axis of the needle results in a plug 72 being removed from the container wall and effective sealing being created between the needle 58 and the opening in the container wall. In the form shown in FIG. 6 the closure has a metal end wall 74 and an interiorly disposed resilient gasket 76. As is noted, both the metal end wall 74 and the gasket 76 are deflected upwardly at the region of penetration by the needle and are in resiliently maintained, sealed relationship with respect to the needle shank, the sealing member 66 disposed on upwardly facing supporting surface 64 also cooperates with the metal closure portion 74 to establish a sealed relationship.

Figure 7:
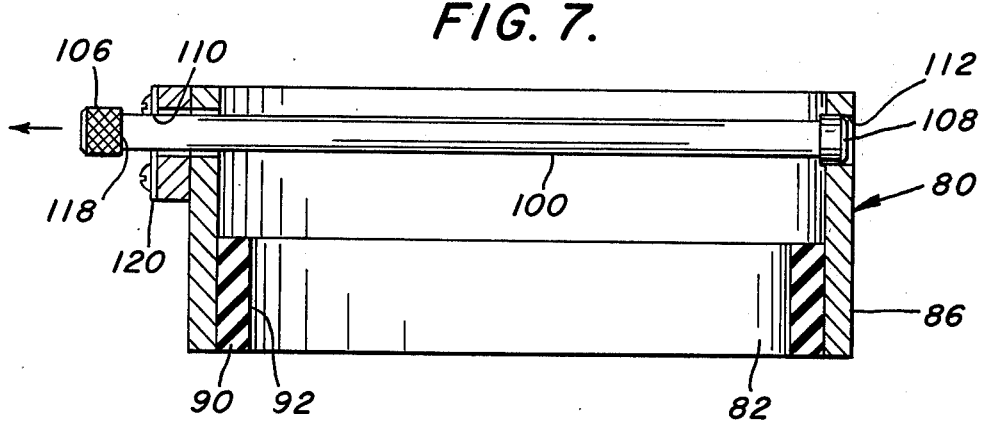
FIG. 7 is a fragmentary cross-sectional illustration of one embodiment of a container retaining member of this invention.
Figure 3:
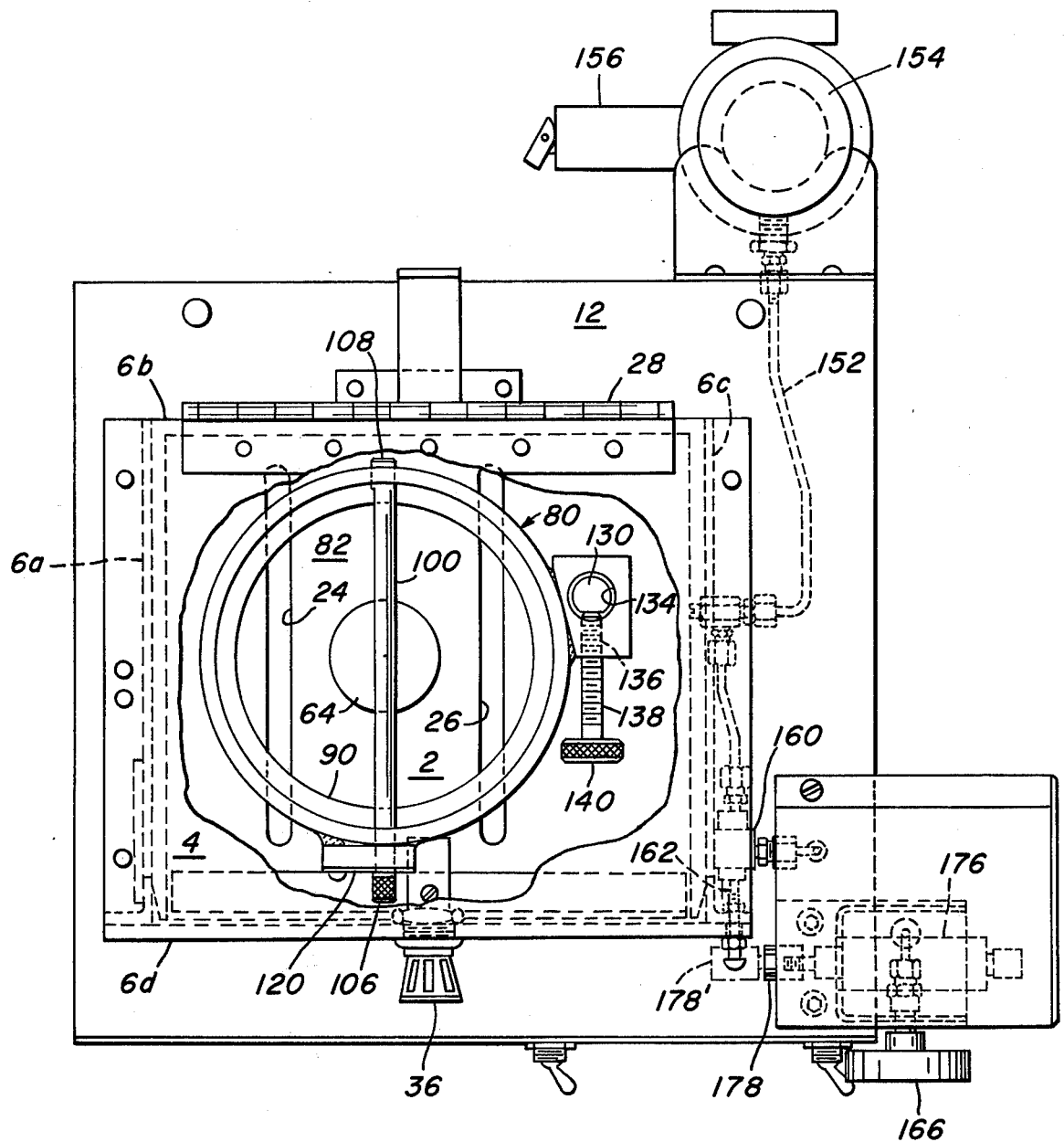
FIG. 3 is a top plan view of the apparatus of FIG. 2 shown without the top wall in place.

Referring now to FIGS. 2, 3 and 7, the container-retaining member 80 will now be considered in greater detail. It will be noted that this member in the form shown has a generally sleeve-like configuration which defines an opening 82 through which the container 50 may be passed when the container is introduced into the container-receiving enclosure. It will be seen that the sleeve portion 86 of the container-retaining member 80 has a lower inner surface within which is received a resilient bushing 90. This bushing 90 has been shown as having its inner surface 92 spaced from the adjacent surface 94 of container 50. In use of the resilient bushing 90 it will generally be preferred to provide a gap of about ⅛ to ⅜ inch between the bushing liner surface 92 and the container surface 94.

Referring still to FIGS. 2, 3 and 7, it is noted that a retaining pin 100 spans the opening 82 defined by retaining member 80. This pin 100 serves to resist undesired upward movement of the sealed container such as might occur when a sealed container fails through closure disengagement from the container. In the form illustrated, the lower portion of pin 100 is spaced at a distance D above surface 102 of container 50. This distance D is preferably greater than zero and such that it does not exceed the distance between the free edge 70 of needle 58 and the closure end wall 60. In this fashion, upward thrust of the bottle will not result in raising of the bottle to such height that it may lift the closure free of the needle with the subsequent dropping of the sealed container resulting in possible damage to needle 58. In general, it is the preferred approach to resist meaningful upward movement of the bottle. The container preferably should not be held rigidly so as to prohibit all upward movement as this could influence the test results.

Looking now at FIGS. 2, 3 and 7, the manner in which a bottle is introduced through retaining member 80 will now be considered. The pin 100 has a handle portion 106, a free end portion 108 and extends through openings 110, 112 in retaining member 80. In the form shown, the pin 100 has been moved slightly from its fully closed position. In removing the pin in order to permit introduction of a sealed container, it is moved in the direction shown by the arrow in FIG. 7. When free end 108 reaches a position which provides sufficient clearance that the sealed container may pass through retaining member 80, further movement need not be effected. The bottle is introduced into the desired position and the pin is replaced by moving the pin to the right in FIG. 7 until the leading surface 118 of handle 106 is in contact with retainer plate 120. It will be appreciated that in order to prevent use of the apparatus when the retainer pin is not in its closed position, door or side wall section 6d is so designed as to be incapable of closing when the pin is not in its fully locked position as the projecting handle 106 will interfere with such closing.

Figure 8:
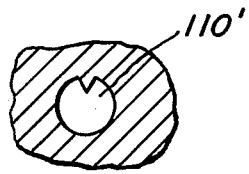
FIGS. 8 and 9 illustrate respectively a rod receiving opening and rod section adapted to cooperate in resisting full rod removal from the container retaining member.
Figure 9:
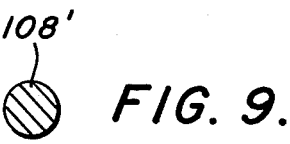

A further hazard could result from the user fully removing the pin so that the assembly could be closed without the sealed container being properly restrained against vertical movement. As a result, it is preferred to provide means for precluding a full removal of the pin. In the form illustrated, the free end 108 of pin 100 is enlarged and of such dimension that it will pass through opening 112 readily, but will not pass through smaller opening 110 in retainer plate 120. An an alternate approach to effecting such limitations, as is shown in FIGS. 8 and 9, the opening 110' in the retainer plate 120' may be provided in the form of a circle with a wedge eliminated and the free end 108' of pin 100' might be provided in full circular shape. The portions of the pin between the handle and the free end may have a shape complimentary to opening 110' so as to permit readily relative movement therebetween. The free end 108' because of its shape is precluded from passing through opening 110' in order to preclude full removal of the pin 100'.

Referring now once again to FIGS. 2 and 3, consideration will be given to the adjusting means employed to adjust the height of the container-retaining member 80 so that it may readily establish the desired distance D, and be located securely in that position. In the form shown, a vertically mounted post 130 has its lower end secured to base wall 2 and is adapted to cooperate with portion 132 of retaining member 80. It is noted that portion 132 has a generally vertically extending bore 134 through which post 130 passes. It is further noted that portion 132 has a passageway 136 oriented generally perpendicularly with respect to bore 134. In the form shown, passageway 134 receives a bolt member 138, which has a head 140 in order to permit convenient manaul adjustment of the container-retaining member 80. Bolt 138 has exterior threads which are adapted to be threadedly engaged within threads in passageway 136 so as to permit locking and unlocking of the post 130 to secure the container-retaining member 80 with respect to the post 130 at any desired vertical location. In this fashion, the container-retaining member 80 may be secured at a desired spaced position in overlying relationship with respect to pedestal 62 to establish distance D.

Turning now to FIGS. 2, 3 and 4, the pressurized fluid handling system will now be considered. A source of pressurized fluid which may conveniently and generally be an air compressor 150 is in communication with the needle 58 by means of a number of fluid conduit sections 152. A pressure regulator 154 which is provided with a relief valve 156 and pressure gauge 155 serves to control the pressure level of the fluid being supplied to the needle and, as a result, to the sealed container interior. A needle valve 158 serves to regulate the speed at which pressure within the sealed container is built up to the desired level. Element 160 is a two-way valve which is adapted to be actuated by mechanical contact between door 6d and plunger 162. The outward position of plunger 162 places the valve in a position which precludes the passage of pressurized fluid from the needle valve therethrough. This means that unless the door is in closed position, no pressure buildup within the sealed container is permitted. With the door in closed position, the operator may then place valve 164 in such position that the pressurized fluid will flow toward needle 58. The pressure gauge 166 provides a direct readout of the internal pressure within the sealed container at any given time. It has been found advantageous to employ a pressure gauge 166 having, in addition to the hand which provides a reading of the existing pressure within the sealed container, a maximum pressure reading hand. This latter hand remains at the reading of maximum pressure recorded during the test until the operator releases the hand. This provides a tangible reading as to the maximum pressure which the sealed container successfully handled or, in the case of failure, the pressure at which failure occurred.

In the embodiment which provides for a transparent wall in the container receiving enclosure, the operator is then permitted to view the sealed container and the pressure level and either determine that the sealed container effectively withstood certain pressure levels or to permit the pressure to continue to rise so that the pressure level at the point of failure may be recorded. Valve 168 is employed in those situations where the sealed container has not fractured during the test. During testing, no pressurized fluid is permitted to emerge through the valve to the surrounding atmosphere. This valve serves as a means for withdrawing pressurized fluid from the sealed container after the test has been completed so as to restore the container to some lower level of pressure.

The check valve 170 is preferably provided so as to prevent reverse flow of the pressurized flow from the sealed container toward the source of pressurized fluid 150.

Tee 172 has one outlet going toward the needle, a second outlet going to the pressure gauge 166 and a third outlet going to cylinder 176. Cylinder 176 serves to prevent opening of door 6d when the sealed container is at an undesired high level of internal pressure. This cylinder 176 has a piston 178 which may be spring operated such that in the position shown in FIG. 3 the spring is retaining the piston 178 in non-interfering relationship with respect to door 6d. When, however, container pressure gets up to the predetermined level, the fluid pressure overcomes the spring resistance and moves the piston 178 to the position shown in a dotted form in FIG. 3 so as to provide a physical barrier to opening of the door 6d.

Referring once again to FIG. 4, it is noted that an orifice 169 is provided between needle 58 and valve 168. This orifice may generally be considered as a plug in the exhaust line to valve 168, with the plug having a small hole (not shown) provided in a conventional manner, as by drilling. This hole is slightly smaller than the opening in needle 58. It is preferred to provide this hole orifice 169 as a safety precaution. Were this not present, it will be appreciated that as soon as exhaust valve 168 were opened, the air pressure in cylinder 40 and pressure gauge 166 would return to atmospheric pressure almost immediately, while the pressure in the container would be reduced more slowly as it would be metered out through the small diameter needle hole. As a result, the cylinder 40 would have its plunger 152 retracted so that the cover could be opened while there was still high internal pressure within the sealed container. As the apparatus will frequently be operated at pressures from about 25 to 300 psi, this could create a serious hazard. With the opening in the orifice 169, however, the exhaust flow is restricted so that pressure in the entire system drops simultaneously.

For purposes of convenience herein, the sealed container has been shown as being a glass or plastic bottle having a metal closure secured thereto. While this invention is in fact uniquely suited to provide benefits in connection with bottles and jars to which various types of closures have been affixed, it will be appreciated that the invention is not so limited and it may be employed with a wide range of containers including food and beverage containers, such as metal and composite cans, for example, and can be readily tested with the present apparatus and method.

In operating the system, the user need merely employ knob 36 to raise the front door 6d and top wall 4. Pin 100 is then moved to an open position and the container is placed in inverted position (in the case of a bottle or jar) upon the needle and is pushed downwardly until the needle penetrates the end wall. The pin 100 may then be restored to its locked position and by means of bolt 138, the container-retaining member may be moved to the desired elevation such that a distance D, which is less than the distance between the container end wall exterior through which the needle has been passed and the free end of the needle. The door 6d is then placed in closed position. While not shown in the drawings, it will be appreciated that if desired, a suitable latch device may be provided on door 6d such that it may readily be operated by grasping knob 36. In this fashion, retention of the closed door will not depend solely upon cylinder 176. The latch may be of the type that simple rotation provides mechanical interference interlock which precludes opening or could be of magnetic or leaf spring retained type. The pressure regulator is then set for the desired upper limit and opening of valve 164 allows flow of pressurized fluid through liner 152 into needle 58 and into sealed container 50. When the pressure within the sealed container exceeds a predetermined level, cylinder 168 will have piston 178 moved to a position which locks the door 6d. Undesired reverse flow is prevented by check valve 170. In the event of container or seal failure, the liquid within the container will flow through drain openings 24, 26 in base wall 2 and be collected in underlying pan 20. Similarly, the pressure will become equalized through holes 24, 26. In the event that the container has not failed during the test, valve 168 may be operated so as to exhaust the built-up pressure to the surrounding atmosphere. Throughout the proceeding the pressure gauge 166 may be monitored so as to provide a meaningful indication of the pressure level within the container.

It will be appreciated that the above described method and apparatus provides a safe, economically feasible, reliable means of determining the security of both a container seal and a container at various predetermined levels of internal pressure. All of this is accomplished in an efficient fashion without the need for cumbersome container distortions, thereby permitting the user periodically to sample commercial merchandise from a production line and determine the effectiveness of the sealed container.

While for convenience of reference herein, use has been made of terms regarding orientation such as "upwardly" and "downwardly" and the like, these terms shall not be deemed limiting of the invention disclosed herein unless the context compels such interpretation.

Whereas various embodiments of the invention have been described as such for purposes of illustration, it will be evidenced to those skilled in the art that numerous variations of the details may be made without departing from the invention as described in the appended claims.

What is claimed is:

1. A pressure testing apparatus for sealed rigid containers comprising:
    a container receiving enclosure defined by a base wall, at least one side wall and a top wall,
    a container supporting pedestal positioned within said container receiving enclosure and having an upwardly facing container supporting surface,
    a needle projecting from said container supporting pedestal,
    pressurized fluid supply means,
    fluid carrying lines providing communication with said pressurized fluid supply means and said needle,
    pressure controlling means interposed between said fluid supply means and said needle,
    a container retaining member disposed within said container receiving enclosure in spaced overlying relationship with respect to said container supporting pedestal, said container retaining member having an elongated bore, an internally threaded passageway oriented generally transversely with respect to said bore and in communication therewith, and a locking bolt threadably engaged within said passageway, and
    container retaining member adjustment means for permitting movement of said container retaining member to provide the desired position with respect to a specific container, said adjustment means having a post portion extending through said bore of said container retaining member, said locking bolt within said passageway of said container retaining member adapted to move into and out of locking engagement with said post to secure said container retaining member to said post.

2. The pressure testing apparatus of claim 1 wherein the projecting free end of said needle has an annular edge disposed within a plane generally perpendicular to the longitudinal axis of said needle.

3. The pressure testing apparatus of claim 1 including said pressure controlling means including a pressure regulator and cooperating needle valve for controlling the pressure of said fluid and the rate at which said fluid is introduced into said container, and
    a pressure gauge communicating with said lines providing a readout of the internal pressure within said container.

4. The pressure testing apparatus of claim 3 including,
    a check valve disposed within said fluid carrying lines preventing undesired passage of fluid from said needle to said pressurized fluid supply means and valve means for controlling flow of said pressurized fluid through said pressure regulator and said needle valve to said needle.

5. The pressure testing apparatus of claim 1 including said pressurized fluid means is an air supply means.

6. The pressure testing apparatus of claim 1 including at least one drain opening provided in said base wall to permit communication between said container receiving enclosure and the exterior thereof.

7. The pressure testing apparatus of claim 1 including,
    a sealing gasket disposed on said container supporting surface of said container supporting pedestal.

8. A pressure testing apparatus for sealed rigid containers comprising:
    a container receiving enclosure defined by a base wall, at least one side wall and a top wall,
    a container supporting pedestal positioned within said container receiving enclosure and having an upwardly facing container supporting surface,
    a needle projecting from said container supporting pedestal,
    pressurized fluid supply means,
    fluid carrying lines providing communication with said pressurized fluid supply means and said needle,
    pressure controlling means interposed between said fluid supply means and said needle,
    a container retaining member disposed within said container receiving enclosure in spaced overlying relationship with respect to said container supporting pedestal, said container retaining member having a generally sleeve-like configuration, said sleeve having a pair of aligned openings in generally diametrically opposed positions, and a container restraining pin received within said openings and extending across said sleeve, and
    container retaining member adjustment means for permitting movement of said container retaining member to provide the desired position with respect to a specific container, said adjustment means having a post portion.

9. The pressure testing apparatus of claim 8 including,
    means permitting removal of said container restraining pin from one said sleeve opening but resisting removal thereof from said container retaining member.

10. The pressure testing apparatus of claim 8 including,
    an annular resiliently compressible bushing disposed within the interior of said container retaining member.

11. A pressure testing apparatus for sealed rigid containers comprising:
    a container receiving enclosure defined by a base wall, at least one side wall and a top wall, said top wall being hingedly secured to said side wall to permit introduction of a sealed container into said container receiving enclosure,
    a sidewall door secured to said hinged top wall and adapted to be moved therewith to establish a sidewall opening in said pressure testing apparatus,
    a container supporting pedestal positioned within said container receiving enclosure and having an upwardly facing container supporting surface,
    a needle projecting from said container supporting pedestal, pressurized fluid supply means, fluid carrying lines providing communication with said pressurized fluid supply means and said needle, pressure controlling means interposed between said fluid supply means and said needle, side wall door-activated switch means preventing passage of pressurized fluid through said pressurized fluid lines to said needle when said sidewall door is in an open position, a container retaining member disposed within said container receiving enclosure in spaced overlying relationship with respect to said container supporting pedestal, and container retaining member adjustment means for permitting movement of said container retaining member to provide the desired position with respect to a specific container.

12. The pressure testing apparatus of claim 11 including a relief valve member permitting exhaust of pressure from said test container after a test has been completed but prior to opening of said door.

13. A pressure testing apparatus for sealed rigid containers comprising:

a container receiving enclosure defined by a base wall, at least one side wall and a top wall, said top wall being hingedly secured to said side wall to permit introduction of a sealed container into said container receiving enclosure, at least one side wall door being adapted for opening to permit access to the interior of said container receiving enclosure, a container supporting pedestal positioned within said container receiving enclosure and having an upwardly facing container supporting surface, a needle projecting from said container supporting pedestal, pressurized fluid supply means, fluid carrying lines providing communication with said pressurized fluid supply means and said needle, pressure controlling means interposed between said fluid supply means and said needle, said pressure controlling means including cylinder means operably responsive to pressure within said sealed container to prevent opening of said side wall door when the pressure within said sealed container exceeds a predetermined level, a container retaining member disposed within said container receiving enclosure in spaced overlying relationship with respect to said container supporting pedestal, and container retaining member adjustment means for permitting movement of said container retaining member to provide the desired position with respect to a specific container.

* * * * *